United States Patent
Olmarker et al.

(10) Patent No.: US 6,649,589 B1
(45) Date of Patent: Nov. 18, 2003

(54) USE OF CERTAIN DRUGS FOR TREATING NERVE ROOT INJURY

(75) Inventors: Kjell Olmarker, Mölndal (SE); Björn Rydevik, Göteborg (SE)

(73) Assignee: A+ Science AB (publ), Göteborg (SE)

( * ) Notice: Subject to any disclaimer, the term of this patent is extended or adjusted under 35 U.S.C. 154(b) by 0 days.

(21) Appl. No.: 09/743,852

(22) PCT Filed: Sep. 23, 1999

(86) PCT No.: PCT/SE99/01671

§ 371 (c)(1),
(2), (4) Date: Jan. 17, 2001

(87) PCT Pub. No.: WO00/18409

PCT Pub. Date: Apr. 6, 2000

(30) Foreign Application Priority Data

Sep. 25, 1998 (SE) .............................................. 9803276
Oct. 29, 1998 (SE) .............................................. 9803710

(51) Int. Cl.$^7$ ........................ A61K 38/00; A61K 31/65
(52) U.S. Cl. .............................. 514/2; 514/152; 530/350
(58) Field of Search ...................... 514/152, 2; 530/350

(56) References Cited

U.S. PATENT DOCUMENTS

| | | | |
|---|---|---|---|
| 4,666,897 A | 5/1987 | Golub et al. | ................ 514/152 |
| 4,925,833 A | 5/1990 | McNamara et al. | ........ 514/152 |
| 5,703,092 A | 12/1997 | Xue et al. | .................... 514/303 |
| 6,015,557 A | 1/2000 | Tobinick et al. | .......... 424/134.1 |
| 6,177,077 B1 | 1/2001 | Tobinick | |
| 6,319,910 B1 * | 11/2001 | Amin et al. | ................. 514/152 |
| 2001/0004456 A1 | 6/2001 | Tobinick | |
| 2001/0016195 A1 | 8/2001 | Tobinick | |
| 2001/0026801 A1 | 10/2001 | Tobinick | |

FOREIGN PATENT DOCUMENTS

| | | |
|---|---|---|
| DE | 4028487 | 3/1992 |
| DE | 4219626 | 12/1993 |
| WO | 95/05363 | 2/1995 |
| WO | 97/06158 | 2/1997 |
| WO | 97/36871 | 10/1997 |
| WO | 98/24766 | 6/1998 |
| WO | 98/34919 | 8/1998 |

OTHER PUBLICATIONS

Wang et al., "Production of Tumor Necrosis Factor in Spinal Cord Following Traumatic Injury in Rats," Journal of Neuroimmunology, 69 (1) 151–156 (1996) Elsevier Science, Ireland.

Sommer et al., "A Metalloprotease–Inhibitor Reduces Pain Associated Behavior in Mice with Experimental Neuropathy." Neuroscience Letters, 237 (1) 45–48 (1997) Elsevier Science, Ireland.

Björn Rydevik et al., "Effects of Graded Compression and Nucleus Pulposus on Nerve Tissue: An Experimental Study in Rabbits", Acta Orthop Scand, 1983, pp. 670–671, vol. 54, No. 1, Taylor & Francis, London, England.

Mamoru Kawakami et al., "mRNA Expression of Interleukins, Phospholipase A$_2$, and Nitric Oxide Synthase in the Nerve Root and Dorsal Root Ganglion Induced by Autologous Nucleus Pulposus In the Rat", Journal of Orthopaedic Research, The Journal of Bone and Joint Surgery, Inc., 1999, pp. 941–946, vol. 17, Orthopaedic Research Society, Rosemont, IL, USA.

U. Schlumpf et al., "Acute Lumbar Disk Displacement with Nerve Root Compression. Indications for Peridural Steroid Injection", *Schweizerische Rundschau Fur Medizin Praxis*, (Feb. 18, 1997) 86 (8) 292–5 (Abstract of STN International, File MEDLINE, Accession No. 97218877).

S. Schienk et al., "Intrathecal Cortison Injection in Lumbar Disc Problems", *Archiv Fur Orthopadische Und Unfall–Chirurgie*, (Jun. 18, 1976) 85 (1) 21–31 (Abstract of STN International, File MEDLINE, Accession No. 76231109).

D. Pennica et al., "Cardiotrophin–1, a Cytokine Present in Embryonic Muscle, Supports Long–Term Survival of Spinal Motoneurons", *NEURON*, (Jul. 1996) 17 (1) 63–74 (Abstract of STN International, File Medline, Accession No. 96310878).

C. Sommer et al., "A Metalloprotease–Inhibitor Reduces Pain Associated Behavior in Mice with Experimental Neuropathy", *Neuroscience Letters*, (Nov. 14, 1997) 237 (1) 45–8 (Abstract of STN International, File MIDLINE, Accession No. 98068711).

C. Sommer et al., "The Effect of Thalidomide Treatment on Vascular Pathology and Hyperalgesia Caused by Chronic Constriction in Injury of Rat Nerve", *Pain*, (Jan. 1998) 74 (1) 83–91 (Abstract of STN International, File MIDLINE, Accession No. 98173500).

J. Kraemer et al., "Lumbar Epidural Perineural Injection: A New Technique", *European Spine Journal*, (1997) 6/5 (357–361) (Abstract of STN International, File Medline, Accession No. 97339851).

K. Olmarker et al., "Inflammatogenic Properties of Nucleus Pulposus", *Spine*, Mar. 15, 1995;20(6):665–0 (Abstract of STN International, File Medline, Accession No. 95328017).

K. Olmarker et al., "Tumor Necrosis Factor Alpha and Nucleus–Pulposus–Induced Nerve Root Injury", *SPINE*, (Dec. 1, 1998) 23 (23) 2538–44 (Abstract of STN International, File Medline, Accession No. 99071916).

(List continued on next page.)

*Primary Examiner*—Lorraine Spector
*Assistant Examiner*—Eileen B. O'Hara
(74) *Attorney, Agent, or Firm*—Burns, Doane, Swecker & Mathis, L.L.P.

(57) ABSTRACT

The present invention relates to pharmaceutical compositions for the treatment of spinal disorders caused by the liberation of TNF-α comprising an effective amount of a TNF-α inhibitor, as well as a method for treatment of such disorders, and the use of TNF-α inhibitors in the preparation of pharmaceutical compositions for such treatment.

39 Claims, No Drawings

OTHER PUBLICATIONS

K. Olmarker et al., "Effects of Methylprednisolone on Nucleus Pulposus–Induced Nerve Root Injury", *Spine*, vol. 19, No. 16, pp. 1803–1808 (1994).

W. Mixter et al., "Rupture of the Intervertebral Disc with Involvement of the Spinal Canal", *New England Surgical Society*, vol. 211, No. 6, pp. 210–215, Aug. 1934.

Peter Wehling, "Antizytokine gegen Entzündung und Schmerz" ("Anticytokines against Inflammation and Pain"), Orthopädische Nachrichten, p. 16, Jan. 1998, Biermann Verlag GmbH, Köln, Germany, http://www.arthrose–ischias.de/ftp/presse 2.pdf, translation included.

"Körpereigener Immunstoff soll bei Therapie helfen" ("The Body's Own Toxoids Help in Therapy"). Dec. 12, 1999, http://www.rp–online.de/news/wissenschat/1999–1230/bandscheibenvorfall.html, translation included.

P. Wehling, "The Use of Cytokine Antagonists in the Treatment of Lumbar Radicular Compression: Pathophysiological Background, Safety and 3 Year Clinical Experience", Abstracts from the International Society for the Study of the Lumpar Spine conference held in Adelaide, Australia, Apr. 9–13, 2000.

Wehling et al., Information Orthokin, "Die Behandlung von Eshias, Arthrose und Rheumatoider Arthrisis mit Orthokin®", Wissenschaftliche Informationen (Patient Information Paper), relevant portions translated.

Wehling, Wissenschaftliches Programm (Scientific Program), Jun. 18, 1999, "Epidural Injectin with a New, Autologous Interleukin–1 Receptor–Antagonist–Protein (IL–1 ra) at Radicular Compression: Pathophysiology, Safety and Clinical Results", http://medweb.uni–muenster.de/institute/orth/versanstaltungen/99–06–18v.html, relevant portions translated.

\* cited by examiner

USE OF CERTAIN DRUGS FOR TREATING NERVE ROOT INJURY

This application is a National Stage of International Application No. PCT/SE99/01671, filed Sep. 23, 1999 in English, which claims benefit of Swedish applications 9803276-6 and 9803710-04 filed respectively on Sep. 25, 1998 and Oct. 29, 1998 in English.

TECHNICAL FIELD

The present invention relates to the use of a TNF-α inhibitor in the preparation of pharmaceutical compositions for the treatment of nerve root injury, as well as a method for treating nerve root injury.

The object of the present invention is to obtain a possibility to treat nerve root injury induced by disk herniation, which may turn up as radiating pain into the arm or leg (sciatica), by blocking disk related cytokines.

BACKGROUND OF THE INVENTION

Disk herniation is a troublesome disorder, which can cause pronounced pain and muscle dysfuntion, and thereby loss of ability to work. A herniation may occur in any disk in the spine but herniations in the lumbar and the cervical spine are most common. A disk herniation in the cervical spine may induce radiating pain and muscle dysfunction in the arm and herniation in the lumbar spine may induce radiating pain and muscle dysfunction in the leg. The radiating pain in the leg is generally referred to as "sciatica". Disk herniation will cause trouble to a varying degree, and the pain may last for one or two months or in severe cases up to 6 months. The arm or leg pain that can occur as a result of disk herniation can be very intense and may thus affect the individual patient's whole life situation during the sickness period.

U.S. Pat. No. 5,703,092 discloses the use of hydroxamic acid compounds and carbocyclic acids as metalloproteinase and TNF inhibitors, and in particular in treatment of arthritis and other related inflammatory diseases. No use of these compounds for the treatment of nerve root injuries is disclosed or hinted at.

U.S. Pat. No. 4,925,833 discloses the use of tetracyclines to enhance bone protein synthesis, and treatment of osteoporosis.

U.S. Pat. No. 4,666,897 discloses inhibition of mammalian collagenolytic enzymes by tetracyclines. The collagenolytic activity is manifested by excessive bone resorption, periodontal disease, rheumatoid arthritis, ulceration of cornea, or resorption of skin or other connective tissue collagen.

Neither of these latter two documents mentions nerve root injury or the treatment thereof.

DESCRIPTION OF THE PRESENT INVENTION

It has now surprisingly been shown possible to be able to treat nerve root injuries, or at least alleviate the symptoms of nerve root injuries by using a pharmaceutical composition comprising an therapeutically active amount of a TNF-α inhibitor selected from the group consisting of metalloproteinase inhibitors excluding methylprenisolone, tetracyclines including chemically modified tetracyclines, quinolones, corticosteroids, thalidomide, lazaroides, pentoxyphylline, hydroxamic acid derivatives, napthopyrans, soluble cytokine receptors, monoclonal antibodies towards TNF-α, amrinone, pimobendan, vesnarinone, phosphodiesterase III inhibitors, lactoferrin and lactoferrin derived analogous, and melatonin in the form of bases or addition salts together with a pharmaceutically acceptable carrier.

The therapeutically effective amount is a dosage normally used when using such compounds for other therapeutic uses. Many of these drugs are commercially known registered drugs.

Compounds that possess this activity are tetracyclines, such as tetracycline, doxycycline, lymecycline, oxytetracycline, minocycline, and chemically modified tetracyclines dedimethylaminotetracycline, hydroxamnic acid compounds, carbocyclic acids and derivatives, thalidomide, lazaroides, pentoxyphylline, napthopyrans, soluble cytokine receptors, monoclonal antibodies towards TNF-α, amrinone, pimobendan, vesnarinone, phosphodiesterase III inhibitors, lactoferrin and lactoferrin derived analogous, melatonin, norfloxacine, ofloxacine, ciprofloxacine, gatifloxacine, pefloxacine, lomefloxacine, and temafloxacine. These can be present as bases or in the form of addition salts, whichever possesses the best pharmaceutical effect, and best property to be brought into a pharmaceutical suitable composition.

After previously being considered as just a biologically inactive tissue component compressing the spinal nerve root at disc herniation, the nucleus pulposus has recently been found to be highly active, inducing both structural and functional changes in adjacent nerve roots when applied epidurally (24, 37, 38, 41, 42). It has thereby been established that autologous nucleus pulposus may induce axonal changes and a characteristic myelin injury (24, 38, 41, 42), increased vascular permeability (9, 44), intra vascular coagulation (24, 36), and that membrane-bound structure or substances of the nucleus pulposus-cells are responsible for these effects (24, 37). The effects have also been found to be efficiently blocked by methyl-prednisolone and cyclosporin A (2, 38). When critically looking at these data, one realizes that there is at least one cytokine that relates to all of these effects, Tumor Necrosis Factor alpha (TNF-α). Further, the active component comprises a substance inhibiting a compound triggered by the release of TNF-α, such as interferon-gamma, interleukin-1, and nitrogen oxide (NO) in the form of base or addition salts.

The invention further relates to a method for inhibiting the symptoms of nerve root injury.

The effects of doxycycline, soluble cytokine-receptors, and monoclonal cytokine-antibodies have been studied and the methods used and results obtained are disclosed below.

EXAMPLE

Study Design

The effects of nucleus pulposus and various treatments to block TNF-α activity were evaluated in an experimental set-up using immunohistochemistry and nerve conduction velocity recordings.

SUMMARY OF BACKGROUND DATA

A meta-analysis of observed effects induced by nucleus pulposus reveals that these effects might relate to one specific cytokine, Tumor Necrosis Factor alpha (TNF(α).

Objectives

To assess the presence of TNF(α) in pig nucleus pulposus cells and to see if blockage of TNF(α) also blocks the nucleus pulposus-induced reduction of nerve root conduction velocity.

Methods

Series-1
Cultured nucleus pulposus-cells were immunohistologically stained with a monoclonal antibody for TNF(α).

Series-2
Nucleus pulposus was harvested from lumbar discs and applied to the sacrococcygeal cauda equina in 13 pigs autologously. Four pigs received 100 mg of doxycycline intravenously, 5 pigs had a blocking monoclonal antibody to TNF-α applied locally in the nucleus pulposus, and 4 pigs remained non-treated and formed control. Three days after the application the nerve root conduction velocity was determined over the application zone by local electrical stimulation.

Series-3
Thirteen pigs had autologous nucleus pulposus placed onto their sacrococcygeal cauda equina similar to series-2. Five pigs (bodyweight 25 kg) received REMICADE (infliximab) 100 mg i.v. preoperatively, and 8 pigs received ENBREL (etanercept) 12.5 mg s.c. preoperatively and additionally 12.5 mg s.c. three days after the operation. Seven days after the nucleus pulposus-application the nerve root conduction velocity was determined over the application zone by local electrical stimulation according to series-2.

Results

Series-1
TNF-α was found to be present in the nucleus pulposus-cells.

Series-2
The selective antibody to TNF-α limited the reduction of nerve conduction velocity, although not statistically significantly to the control series. However, treatment with doxycycline significantly blocked the nucleus pulposus-induced reduction of conduction velocity.

Series-3
Both drugs (infliximab, and etanercept) blocked the nucleus pulposus induced nerve injury efficiently and normal average nerve conduction velocities were found after treatment with both of these two drugs.

Conclusion

For the first time a specific substance, Tumor Necrosis Factor-alpha, has been linked to the nucleus pulposus-induced effects of nerve roots after local application. Although the effects of this substance may be synergistic with other similar substances, the data of the present study may be of significant importance for the continued understanding of nucleus pulposus' biologic activity, and might also be of potential use for future treatment strategies of sciatica.

After previously being considered as just a biologically inactive tissue component compressing the spinal nerve root at disc herniation, the nucleus pulposus has recently been found to be highly active, inducing both structural and functional changes in adjacent nerve roots when applied epidurally (24, 37, 38, 41, 42). It has thereby been established that autologous nucleus pulposus may induce axonal changes and a characteristic myelin injury (24, 38, 41, 42), increased vascular permeability (9, 44), intra vascular coagulation (24, 36), and that membrane-bound structure or substances of the nucleus pulposus-cells are responsible for these effects (24, 37). The effects have also been found to be efficiently blocked by methyl-prednisolone and cyclosporin A (2, 38). When critically looking at these data, one realizes that there is at least one cytokine that relates to all of these effects. Tumor Necrosis Factor alpha (TNF-α). To assess if TNF-α may be involved in the nucleus pulposus induced nerve root injury, the presence of TNF-α in nucleus pulposus-cells was assessed by studying if the nucleus pulposus-induced effects could be blocked by doxycycline, a soluble TNF-receptor, and a selective monoclonal TNF-antibody, The latter was administered both locally in the nucleus pulposus and systemically.

MATERIAL AND METHODS

Series-1, Presence of TNF-α in Pig Nucleus Pulposus-cells

Nucleus pulposus (NP) from a total of 13 lumbar and thoracic discs were obtained from a pig used for other purposes. NP was washed once in Ham's F12 medium (Gibco BRL, Paisley, Scotland) and then centrifuged and suspended in 5 ml of collagenase solution in Ham's F12 medium (0.8 mg/ml, Sigma Chemical Co., St Louis, Mo., USA) for 40 minutes, at 37° C. in 25 cm$^2$ tissue culture flasks. The separated NP-cell pellets were suspended in DMEM/F12 1:1 medium (Gibco BRL, Paisley, Scotland) supplemented with 1% L-glutamine 200 mM (Gibco BRL, Paisley, Scotland), 50 Mg/ml gentamycine sulphate (Gibco BRL, Paisley, Scotland) and 10% foetal calf serum (FCS), (Gibco BRL, Paisley, Scotland). The cells were cultured at 37° C. and 5% $CO_2$ in air for 3–4 weeks and then cultured directly on tissue culture treated glass slides (Becton Dickinson & Co Labware, Franklin Lakes, N.J., USA). After 5 days on the glass slides, the cells were fixed in situ by acetone for 10 minutes. After blocking irrelevant antigens by application of 3% $H_2O_2$ (Sigma Chemical Co., St Louis, Mo., USA) for 30 minutes and Horse Serum (ImmunoPure ABC, peroxidase mouse IgG staining kit nr.32028, Pierce, Rockford, Ill.) for 20 minutes, the primary antibody (Anti-pig TNF-α monoclonal purified antibody, Endogen, Cambridge, Mass., USA) was applied over night at +40° C., diluted at 1:10, 1:20 and 1:40. For control, BSA (bovine serum albumin, Intergen Co, New York, USA) suspended in PBS (phosphate buffered saline, Merck, Darmstadt, Germany) was applied in the same fashion. The next day the cells were washed with 1% BSA in PBS and the secondary antibody (Immunopure ABC, peroxidase mouse IgG staining kit nr.32028, Pierce, Rockford, Ill.) was applied for 30 minutes. To enhance this reaction, the cells were exposed to Avidin-Biotin complex for additionally 30 minutes (ImmunoPure ABC, peroxidase mouse IgG staining kit nr.32028, Pierce, Rockford, Ill.). The cells were then exposed to 20 mg of DAB (3,3-diaminobenzidine tetrahydrochloride nr. D-5905, Sigma Chemical Co., St Louis, Mo., USA) and 0.033 ml of 3% $H_2O_2$ in 10 ml of saline for 10 minutes. The cells were washed in PBS, dehydrated in a series of ethanol, mounted and examined by light microscopy by an unbiased observer regarding the presence of a brown colouration indicating presence of TNF-α.

Series-2, Neurophysiologic Evaluation

Thirteen pigs, (body weight 25–30 kg) received an intramuscular injection of 20 mg/kg body weight of KETALAR® (ketamine 50 mg/ml, Parke-Davis, Morris Plains, N.J.) and an intravenous injection of 4 mg/kg body weight of Hypnodil$^R$ (methomidate chloride 50 mg/ml, A B Leo, Helsingborg, Sweden) and 0.1 mg/kg body weight of STRESNIL® (azaperon 2 mg/ml, Janssen Pharmaceutica, Beerse, Belgium). Anaesthesia was maintained by additional intravenous injections of 2 mg/kg body weight of HYPNODIL® and 0.05 mg/kg body weight of STRESNIL®. The pigs also received an intravenous injection of 0.1 mg/kg of STESOLID® NOVUM® (Diazepam, Dumex, Helsingborg, Sweden) after surgery.

Nucleus pulposus was harvested from the 5th lumbar disc through a retro peritoneal approach (42). Approximately 40 mg of the nucleus pulposus was applied to the sacrococcygeal cauda equina through a midline incision and laminectomy of the first coccygeal vertebra. Four pigs did not receive any treatment (no treatment). Four other pigs received an intravenous infusion of 100 mg of doxycycline (Vibramycino, Pfizer Inc., New York, USA) in 100 ml of saline over 1 hour. In 5 pigs, the nucleus pulposus was mixed with 100 µl of a 1.11 mg/ml suspension of the anti-TNF-α antibody used in Series 1, before application.

Three days after the application, the pigs were reanaesthetized by an intramuscular injection of 20 mg/kg body weight of KETALAR® and an intravenous injection of 35 mg/kg body weight of PENTOTHAL® (Thiopental sodium, Abbott lab, Chicago, Ill.). The pigs were ventilated on a respirator. Anaesthesia was maintained by an intravenous bolus injection of 100 mg/kg body weight of Chloralose (α)-D(+)-gluco-chloralose, Merck, Darmstadt, Germany) and by a continuous supply of 30 mg/kg/hour of Chloralose. A laminectomy from the 4th sacral to the 3rd coccygeal vertebra was performed. The nerve roots were covered with SPONGOSTANE® (Ferrosan, Demnark). Local tissue temperature was continuously monitored and maintained at 37.5–38.0° C. by means of a heating lamp.

The cauda equina was stimulated by two E2 subdermal platinum needle electrodes (Grass Instrument Co., Quincy, Mass.) which were connected to a Grass SD9 stimulator (Grass Instrument Co., Quincy, Mass.) and gently placed intermittently on the cauda equina first 10 mm cranial and then 10 mm caudal to the exposed area. To ensure that only impulses from exposed nerve fibres were registered, the nerve root that exited from the spinal canal between the two stimulation sites were cut. An EMG was registered by two subdermal platinum needle electrodes which were placed into the paraspinal muscles in the tail approximately 10 mm apart. This procedure is reproducible and represents a functional measurement of the motor nerve fibres of the cauda equina nerve roots. The EMG was visualized using a Macintosh IIci computer provided with Superscope software and MacAdios II AID converter (GW Instruments, Sommerville, Mass.) together with a Grass P18 preamplifier (Grass Instrument Co., Quincy, Mass.). The separation distance between the first peaks of the EMG from the two recordings was determined and the separation distance between the two stimulation sites on the cauda equina was measured with calipers. The nerve conduction velocity between the two stimulation sites could thus be calculated from these two measurements.

The person performing the neurophysiologic analyses was unaware of the experimental protocol for the individual animal, and after finishing the complete study the data were arranged in the three experimental groups and statistical differences between the groups were assessed by Student's t-test. The experimental protocol for this experiment was approved by the local animal research ethics committee.

Series-3

Thirteen pigs had autologous nucleus pulposus placed onto their sacrococcygeal cauda equina similar, to series-2. Five pigs (bodyweight 25 kg) received the human/murine monoclonal antibody REMICADE® (infliximab, Immunex Corporation, Seattle, Wash. 98101, USA) 100 mg i.v. preoperatively, and 8 pigs received ENBREL® (etanercept, Centocor B.V., Leiden, the Netherlands) 12.5 mg s.c. preoperatively and additionally 12.5 mg s.c. three days after the operation. Seven days after the nucleus pulposus-application the nerve root conduction velocity was determined over the application zone by local electrical stimulation according to series-2. To blind the study the neurophysiological evaluation was conducted in parallel to another study and the person performing the analyses did not know from which study and what treatment each specific animal was subjected to. No non-treated animals were included in the series-3 due to the pre-existing knowledge of nerve conduction velocity after seven days of either nucleus pulposus or fat (control) application. The statistical difference between the groups, infliximab, and etanercept, nucleus pulposus without treatment (positive control from previous data) and application of retroperitoneal fat (negative control from previous data) was assessed by using ANOVA and Fisher's PLSD at 5%.

RESULTS

Series-1, Presence of TNF-α in Pig Nucleus Pulposus-cells

Examples of the light microscopic appearance of the stained glass slides. In the sections using BSA in PBS as "primary antibody" (control) no staining was observed, ensuring that there was no labelling and visualization of irrelevant antigens. When the anti-TNF-α antibody was applied at 1:40 dilution there was only a weak staining. However, the staining increased with diminishing dilutions of the antibody. The staining was seen in the soma of the cells and it was not possible to differentiate whether TNF-α was located in the cytoplasm, on the cell surface bound to the cell-membrane, or both.

Series-2, Neurophysiologic Evaluation

Application of non-modified nucleus pulposus and without any treatment induced a reduction in nerve conduction velocity similar to previous studies (Table 1), whereas treatment with doxycycline completely blocked this reduction ($p<0.01$ Student's t-test). Local application of anti-TNF-α-antibody also induced a partial block of this reduction, although not as complete as doxycycline and not statistically significant to the no treatment-series.

Series-3

Treatment with both drugs seemed to prevent the nucleus pulposus-induced reduction of nerve root conduction velocities since the average nerve conduction velocity for both these treatment groups were close to the average conduction of fat-application series as seen in a previous study (Table 2). There was a statistically significant difference to application of nucleus pulposus, but without any treatment, seen for both drugs.

TABLE 1

| | Series-2 | |
|---|---|---|
| Treatment | n | NCV (m/s + SD) |
| Local anti-TN-α | 5 | 64 ± 28 |
| Doxycycline | 4 | 76 ± 9 |
| No treatment | 4 | 46 ± 12 |

TABLE 2

| | Series-3 | |
|---|---|---|
| Treatment | n | NCV (m/s + SD) |
| Fat* | 5 | 76 ± 11 |
| EMBREL ® | 8 | 78 ± 14 |
| REMICADE ® | 5 | 79 ± 15 |
| No treatment* | 5 | 45 ± 19 |

*Data included from ref. no. 42, Olmarker et al, 1993

DISCUSSION

The data of the present study demonstrated that TNF-α may be found in nucleus pulposus-cells of the pig. If TNF-α was blocked by a locally applied selective monoclonal antibody, the nucleus pulposus-induced reduction of nerve root conduction velocity was partially blocked, although not statistically significant compared to the series with non-treated animals. However, if systemic treatments with doxycycline, infliximab, and etanercept were used to inhibit TNF-α, the reduction of nerve conduction velocity was significantly prevented.

In recent years, it has been verified that local application of autologous nucleus pulposus may injure the adjacent nerve roots. Thus, it has become evident that the nerve root injury seen as disc herniation may not be solely based on mechanical deformation of the nerve root, but may also be induced by unknown "biochemical effects" related to the epidural presence of herniated nucleus pulposus. Although this new research field has generated many experimental studies, the mechanisms and substances involved are not fully known. It has been seen that local application of autologous nucleus pulposus may induce axonal injury (24,37,38,40–42), a characteristic injury of the myelin sheath (24,38,40–42), a local increase of vascular permeability (9,36,44), intra vascular coagulations, reduction of intra neural blood flow (43), and leukotaxis (36). It has been seen that the nucleus pulposus-related effects may be blocked efficiently by methylprednisolone (38) and cyclosporin A (2), and slightly less efficiently by indomethacin (3), and lidocaine (69). Further, it has been understood that the effects are mediated by the nucleus pulposus-cells (37), particularly by substances or structures bound to the cell-membranes (25). When critically considering these data, it becomes evident that at least one specific cytokine could be related to these observed effects, Tumor Necrosis Factor-alpha (TNF-α). TNF-α may induce nerve injury (29,31,45,50,66) mainly seen as a characteristic myelin injury that closely resembles the nucleus pulposus-induced myelin-injury (29,47,51,54,62,64,66,70). TNF-αmay also induce an increase in vascular permeability (47,66) and initiate coagulation (22,34,63). Further, TNF-α may be blocked by steroids (4,8,21,61,68), and cyclosporin A (11, 55,67,68). However, the blocking effect on TNF-α is not so pronounced by NSAID (14,17,20) and very low or the opposite by lidocaine (5,32,46,60). It was recently observed that local application of nucleus pulposus may induce pain-related behaviour in rats, particularly thermal hyperalgesia (23,40). TNF-α has also been found to be related to such pain-behaviouristic changes (12,35,56,66), and also to neuropathies in general (30,54,56,57). However there are no studies that have assessed the possible presence of TNF-α in the cells of the nucleus pulposus.

To assess if TNF-α could be related to the observed nucleus pulposus induced reduction in nerve root conduction velocity it was necessary first to analyse if there was TNF-α in the nucleus pulposus-cells. The data clearly demonstrated that TNF-α was present in these cells. TNF-α is produced as precursor (pro-TNF) that is bound to the membrane and it is activated by cleavage from the cell-membrane by a zinc-dependent metallo-endopeptidase (TNF-α converting enzyme, TACE) (6,15,16,48,49). This may thus relate well to experimental findings where application of the mere cell-membranes of autologous nucleus pulposus-cells induced nerve conduction velocity reduction, which indicated that the effects were mediated by a membrane-bound substances. Second, the effects of the TNF-α had to be blocked in a controlled manner. We then first chose to add the same selective antibody that was used for immunohistochemistry in series 1, which is known to also block the effects of TNF-α, to the nucleus pulposus before application.

Also, we chose to treat the pigs with doxycycline, which is known to block TNF-α (26,27,33,52,53). However, due to the low pH of the doxycycline preparation it was chosen to treat the pigs by intravenous injection instead of local addition to the nucleus pulposus since nucleus pulposus at a low pH has been found to potentiate the effects of the nucleus pulposus (38,39).

Two recently developed drugs for specific TNF-α inhibition were also included in the study.

Infliximab is a chimeric monoclonal antibody composed of human constant and murine variable regions, and binds specifically to human TNF-α. As opposed to the monoclonal antibody used in series-2 for the 3 days observation period, infliximab was not administered locally in the autotransplanted nucleus pulposus but instead systemically in a clinically recommended dose (4 mg/kg). Etanercept is a dimeric fusion protein consisting of the Fc portion of human IgG. The drug was administered in a dosage comparable to the recommended dose for pediatric use (0.5 mg/kg, twice a week).

The data regarding nerve conduction velocity showed that the reduction was completely blocked by the systemic-treatment and that the nerve conduction velocities in these series were close to the conduction velocity after application of a control substance (retro peritoneal fat) from a previous study (42). Application of the anti-TNF-α-antibody to the nucleus pulposus also partially prevented the reduction in nerve conduction velocity, however, not as pronounced as doxycycline, and the velocity in this series was not statistically different to the velocity in the series with not treated animals, due to the wide deviation of the data.

The fact that the local anti-TNF-α antibody treatment only partially blocked the nucleus pulposus-induced reduction of nerve conduction velocity and the high standard deviation of the data could probably have at least three different explanations. First, if looking at the specific data within this group it was found that the nerve conduction velocity was low in 2 animals (mean 37.5 m/s) and high in 3 animals (mean 81.3 m/s). There are thus 2 groups of distinctly different data within the anti-TNF-α treatment series. This will account for the high standard deviation and might imply that the blocking effect was sufficient in 3 animals and non-sufficient in 2 animals. The lack of effects in these animals could be based simply on the amount of antibodies in relation to TNF-α molecules not being sufficient, and if a higher dose of the antibody had been used, the TNF-α effects would thus have been blocked even in these animals. Such a scenario could then theoretically imply that TNF-α alone is responsible for the observed nucleus pulposus-induced effects, and that this could not be verified experimentally due to the amount of antibody being too low.

Second, it is also known that tetracyclines such as doxycycline and minocycline may block a number of cytokines and other substances. For instance they may block IL-1 (1,28,58), IFNγ (27), NO-synthetasel, and metalloproteinases (1,53,58). Particularly IL-1 and IFNγ are known to act synergistically with TNF-α and are known to be more or less neurotoxic (7,10,13,18,19,56,59). These substances, are also blocked by steroids and cyclosporin A which corresponds well with the previous observations on nucleus pulposus-induced nerve root injury which have shown that the nucleus pulposus-induced effects may be blocked by these substances (8,67). One may therefore also consider the possibility that a selective block of TNF-α may not be sufficient to completely block the nucleus pulposus-induced effects on nerve function, and that simultaneous block of other synergistic substances is necessary as well. Thus, this scenario, on the other hand, implies that TNF-α is not solely responsible for the nucleus pulposus-induced effects, and that other synergistic substances, which are also blocked by doxycycline, may be necessary.

The third explanation could be that the amount of TNF in the nucleus pulposus may well be enough to start the pathophysiologic cascade locally in the nerve root, comprising increased vascular permeability and aggregation and recruitment of systemic leukocytes. However, it is these leukocytes that have the major content of TNF-α and that systemic treatment in a sufficient dose is necessary to block the contribution from these leukocytes, and thereby also blocking the events leading to nerve injury.

TNF-α may have various pathophysiologic effects. It may have direct effects on tissues such as nerve tissue and blood vessels, it may trigger other cells to produce other pathogenic substances and it may trigger release of more TNF-α both by inflammatory cells and also by Schwann-cells locally in the nerve tissue (65). There is thus reason to believe that even low amounts of TNF-α may be sufficient to initiate these processes and that there is a local recruitment of cytokine producing cells and a subsequent increase in production and release of other cytokines as well as TNF-α. TNF-α may therefore act as the "ignition key" of the pathophysiologic processes and play an important role for the initiation of the pathophysiologic cascade behind the nucleus pulposus-induced nerve injury. However, the major contribution of TNF-α may be derived from recruited, aggregated and maybe even extravasated leukocytes, and that successful pharmacologic block may be achieved only by systemic treatment.

In conclusion, although the exact role of TNF-α can not be fully understood from the experimental set-up, we may conclude that for the first time a specific substance (TNF-α) has been linked to the nucleus pulposus-induced nerve root injury. This new information may be of significant importance for the continued understanding of nucleus pulposus-induced nerve injury as well as raising the question of the potential future clinical use of pharmacological interference with TNF-α and related substances, for treatment of sciatica.

The presence of TNF-α in pig nucleus pulposus-cells was thus immunohistochemically verified. Block of TNF-α by a locally applied monoclonal antibody partially limited the nucleus pulposus-induced reduction of nerve root conduction velocity, whereas intravenous treatment with doxycycline, infliximab, and etanercept significantly blocked this reduction. These data for the first time links one specific substance, TNF-α, to the nucleus pulposus-induced nerve injury.

Aminoguanidine has showed to inhibit the release of nitrogen oxide (NO) at nerve root injuries by inhibiting inducible nitrogen oxide synthetase, and aminoguanidine is thus one compound that inhibits a compound trigged by the release of TNF-α.

The compounds of the invention can be administered in a variety of dosage forms, e.g, orally, in the form of tablets, capsules, sugar or film coated tablets, liquid solutions; rectally, in the form of suppositories; parenterally, e.g., intramuscularly or by intravenous injection or infusion. The therapeutic regimen for the different clinical syndromes must be adapted to the type of pathology taken in to account, as usual, also the route of administration, the form in which the compound is administered and age, weight, and condition of the subject involved.

The oral route is employed, in general, for all conditions, requiring such compounds. In emergency cases preference is given to intravenous injection. For these purposes the compounds of the invention can be administered orally at doses ranging from about 20 to about 1500 mg/day. Of course, these dosage regimens may be adjusted to provide the optimal therapeutic response.

The nature of the pharmaceutical composition containing the compounds of the invention in association with pharmaceutically acceptable carriers or diluents will, of course, depend upon the desired route of administration. The composition may be formulated in the conventional manner with the usual ingredients. For example, the compounds of the invention may be administered in the form of aqueous or oily solutions or suspensions, tablets, pills, gelatine capsules (hard or soft ones)syrups, drops or suppositories.

Thus for oral administration, the pharmaceutical compositions containing the compounds of the invention are preferably tablets, pills or gelatine capsules, which contain the active substance together with diluents, such as lactose, dextrose, sucrose, mannitol, sorbitol, cellulose; lubricants, e.g., silica, talc, stearic acid, magnesium or calcium stearate, and/or polyethylene glycols; or they may also contain binders, such as starches, gelatine, methyl cellulose, carboxymethylcellulose, gum arabic, tragacanth, polyvinylpyrrolidone; disaggregating agents such as starches, alginic acid, alginates, sodium starch glycolate, microcrystalline cellulose; effervescing agents such a carbonates and acids; dyestoffs; sweeteners; wetting agents, such as lecithin, polysorbates, laurylsulphates; and in general non-toxic and pharmaceutically inert substances used in the formulation of pharmaceutical compositions. Said pharmaceutical compositions may be manufactured in known manners, e.g., by means of mixing, granulating, tableting, sugar-coating or film-coating processes. In the case film providing compounds can be selected to provide release in the right place in the intestinal tract with regard to absorption and maximum effect. Thus pH-dependent film formers can be used to allow absorption in the intestines as such, whereby different phthalate are normally used or acrylic acid/methacrylic acid derivatives and polymers.

The liquid dispersions for oral administration may be e.g., syrups, emulsion, and suspensions.

The syrups may contain as carrier, e.g., saccharose, or saccharose with glycerine and/or mannitol and/or sorbitol.

Suspensions and emulsions may contain as carrier, e.g., a natural gum, such as gum arabic, xanthan gum, agar, sodium alginate, pectin, methyl cellulose, carboxymethylcellulose, polyvinyl alcohol.

The suspension or solutions for intramuscular injections may contain together with the active compound, a pharmaceutically acceptable carrier, such as e.g., sterile water, olive oil, ethyl oleate, glycols, e.g., propylene glycol, and if so desired, a suitable amount of lidocaine hydrochloride. Adjuvants for trigging the injection effect can be added as well.

The solutions for intravenous injection or infusion may contain as carrier, e.g., sterile water, or preferably, a sterile isotonic saline solution, as well as adjuvants used in the field of injection of active compounds.

The suppositories may contain together with the active compound, a pharmaceutically acceptable carrier, e.g., cocoa-butter polyethylene glycol, a polyethylene sorbitan fatty acid ester surfactant or lecithin.

REFERENCES

1. Amin A R, Attur M G, Thakker G D, Patel P D, Vyas P R, Patel R N, Patel I R, Abramson S B. A novel mechanism of action of tetracyclines: effects on nitric oxide syntheses. *Proc Natl Acad Sci U S A* 1996; 93:14014–9.
2. Arai I, Konno S, Otani K, Kikuchi S, Olmarker K. Cyclosporin A blocks the toxic effects of nucleus pulposus on spinal nerve roots. Manuscript
3. Arai I, Mao G P, Otani K, Konno S, Kikuchi S, Olmarker K. Indomethacin blocks nucleus pulposus related effects in adjacent nerve roots. Manuscript
4. Baumgartner R A, Deramo V A, Beaven M A. Constitutive and inducible mechanisms for synthesis and release of cytokines in immune cell lines. *J Immunol* 1996;157:4087–93.
5. Bidani A, Heming T A. Effects of lidocaine on cytosolic pH regulation and stimulus-induced effector functions in alveolar macrophages. *Lung* 1997;175:349–61.
6. Black R A, Rauch C T, Kozlosky C J, Peschon J J, Slack J L, Wolfson M F, Castner B J, Stocking K L, Reddy P, Srinivasan S, Nelson N, Boiani N, Schooley K A, Gerhart M, Davis R, Fitzner J N, Johnson R S, Paxton R J, March C J, Cerretti D P. A metalloproteinase disintegrin that releases tumour-necrosis factor-α from cells. *Nature* 1997;385:729–33.
7. Bluthe R M, Dantzer R, Kelley K W. Interleukin-1 mediates behavioural but not metabolic effects of tumor necrosis factor alpha in mice. *Eur J Pharmacol* 1991;209:281–3.
8. Brattsand R, Linden M. Cytokine modulation by glucocorticoids: mechanisms and actions in cellular studies. *Aliment Pharmacol Ther* 1996; 10:81–90,
9. Byröd G, Otani K, Rydevik B, Olmarker K. Acute increase in endoneural vascular permeability induce by epidural application of nucleus pulposus on spinal nerve roots. Manuscript
10. Chao C C, Hu S, Ehrlich L, Peterson P K. Interleukin-1 and tumor necrosis factor-alpha synergistically mediate neurotoxicity: involvement of nitric oxide and of N-methyl-D-aspartate receptors. *Brain Behav Immun* 1995;9:355–65.
11. Dawson J, Hurtenbach U, MacKenzie A. Cyclosporin A inhibits the in vivo production of interleukin-Ibeta and tumour necrosis factor alpha, but not interleukin-6, by a T-cell-independent mechanism. *Cytokine* 1996;8:882–8.
12. DeLeo J A, Colburn R W, Rickman A J. Cytokine and growth factor immunohistochemical spinal profiles in two animal models of mononeuropathy. *Brain Res* 1997;759:50–7.
13. Gadient R A, Cron K C, Otten U. Interleukin-1 beta and tumor necrosis factor-alpha synergistically stimulate nerve growth factor (NGF) release from cultured rat astrocytes. *Neurosci Lett* 1990;117:335–40.
14. Garcia-Vicuna R, Diaz-Gonzalez F, Gonzalez-Alvaro 1, del Pozo M A, Moilinedo F, Cabanas C, Gonzalez-Amaro R, Sanchez-Madrid F. Prevention of cytokine-induced changes in leucocyte adhesion receptors by nonsteroidal antiinflammatory drugs from the oxicam family. *Arthritis Rheum* 1997;40:143–53.
15. Gearing A J, Beckett P, Christodoulou M, Churchill M, Clements J, Davidson A H, Drummond A H, Galloway W A, Gilbert R, Gordon J L, et al. Processing of tumour necrosis factor-alpha precursor by metalloproteinases. *Nature* 1994;370:555–7.
16. Gazelle E J, Banda M J, Leppert D. Matrix metalloproteinases in immunity. *J Immunol* 1996; 156:14.
17. Gonzalez E, de la Cruz C, de Nicolas R, Egido J, Herrero-Beaumont G. Long-term effect of nonsteroidal anti-inflammatory drugs on the production of cytokines and other inflammatory mediators by blood cells of patients with osteosis. *Agents Actions* 1994;41:171–8.
18. Hartung H P, Jung S, Stoll G, Zielasek J, Schmidt B, Archelos J J, Toyka K V. Inflammatory mediators in demyelinating disorders of the CNS and PNS. *J Neuroinununol* 1992;40:197–210.
19. Hattori A, Iwasald S, Murase K, Tsujimoto M, Sato M, Hayashi K, Kohno M. Tumor necrosis factor is markedly synergistic with interleukin I and ii3terferon-gamma in stimulating the production of nerve growth factor in fibroblasts. *FEBS Lett* 1994;340:177–80.
20. Herman J H, Sowder W G, Hess E V. Nonsteroidal antiinflammatory drug modulation of prosthesis pseudomembrane induced bone resorption. *J Rheunutol* 1994;21:338–43.
21. Iwamoto S, Takeda K. [Possible cytotoxic mechanisms of TNF in vitro]. *Hum Cell* 1990;3:107–12.
22. Jurd K M, Stephens C J, Black M M, Hunt B J. Endothelial cell activation in cutaneous vasculitis. *Clin Exp Dermatol* 1996;21:28–32.
23. Kawakami M, Tamaki T, Weinstein J N, Hashizume H, Nishi H, Meller S T. Pathomechanism of pain-related behaviour produced by allografts of intervertebral disc in the rat. *Spine* 1996;21:2101–7.
24. Kayama S, Konno S, Olmarker K, Yabuki S, Kikuchi S. Incision of the anulus fibrosis induces nerve root morphologic, vascular, and functional changes. An experimental study. *Spine* 1996;21:2539–43.
25. Kayama S, Olmarker K, Larsson K, Sjögren-Jansson E, Lindahl A, Rydevik B. Cultured, autologous nucleus pulposus cells induce structural and functional changes in spinal nerve roots. *Spine,* 1998, 23:90:2155–58,
26. Kloppenburg M, B~an B M, de Rooij-Dijk H H, Miltenburg A M, Daha M R, Breedveld F C, Dijkmans B A, Verweij C. The tetracycline derivative minocycline differentially affects cytokine production by monocytes and T lymphocytes. *Antimicrob Agents Chemother* 1996;40:934–40.
27. Kloppenburg M, Verweij C L, Miltenburg A M, Verboeven A J, Daha M R, Dijkmans B A, Breeveld F C. The influence of tetracyclines on T cell activation. *Clin Exp Immunol* 1995;102:635–41.
28. Lamster I B, Pullman J R, Celenti R S, Grbic J T. The effect of tetracycline fiber therapy on beta-glucuronidase and interleukin-1 beta in crevicular fluid. *J Clin Periodontol* 1996;23:816–22.
29. Liberski P P, Yanagihara R, Nerurkar V, Gajdusek D C. Further ultrastructural studies of lesions induced in the optic nerve by tumor necrosis factor alpha (TNF-α): a comparison with experimental Creutzfeldt-Jakob disease. *Acta Neurobiol Exp (Warsz)* 1994;54:209–18.
30. Lin X H, Kashima Y, Khan M, Heller K B, Gu X Z, Sadun A A. An immunohistochemical study of TNF-α in optic nerves from AIDS patients. *Curr Eye Res* 1997;16:1064–8.
31. Madigan M C, Sadun A A, Rao N S, Dugel P U, Tenhula W N, Gill P S. Tumor necrosis factor-alpha (TNF-α)-induced optic neuropathy in rabbits. *Neurol Res* 1996; 18:176–84.
32. Matsumori A, Ono K, Nishio R, Nose Y, Sasayama S. Amiodarone inhibits production of tumor necrosis factor-alpha by human mononuclear cells: a possible mechanism for its effect in heart failure. *Circulation* 1997;96:1386–9.
33. Milano S, Arcoleo F, D'Agostino P, Cillari E. Intraperitoneal injection of tetracyclines protects mice from lethal endotoxemia downregulating inducible nitric oxide syn- 33. thase in various organs and cytokine and nitrate secretion in blood. *Antimicrob Agents Chemother* 1997;41:117–21.
34. Nawroth P, Handley D, Matsueda G, De Waal R, Gerlach H, Blohm D, Stem D. Tumor necrosis factor/cachectin-induced intra vascular fibrin formation in meth A fibrosarcomas. *J Exp Med* 1988;168:637–47.
35. Oka T, Wakugawa Y, Hosoi M, Oka K, Hori T. Intracerebroventricular injection of tumor necrosis factor-alpha induces thermal hyperalgesia in rats. *Neuroimmunomodulation* 1996;3:135–40.
36. Olmarker K, Blomquist J, Stromberg J, Nannmark, U, Thomsen P, Rydevik B. Inflamma-togenic properties of nucleus pulposus. *Spine* 1995;20:665–9.
37. Olmarker K, Brisby H, Yabuki S, Nordborg C, Rydevik B. The effects of normal, frozen, and hyaluronidase-digested nucleus pulposus on nerve root structure and function. *Spine* 1997;22:4715; discussion 476.
38. Olmarker K, Byrod G, Comefjord M, Nordborg C, Rydevik B. Effects of methylprednisolone on nucleus pulposus-induced nerve root injury. Spine 1994; 19:1803–8.
39. Olmarker K, lwabuchi M, Larsson K, Rydevik B. Effects of in vitro degenerated nucleus pulposus on nerve root conduction velocity. Manuscript
40. Olmarker K, Myers R R. Pathogenesis of sciatic pain: Role of herniated nucleus pulposus and deformation of spinal nerve root and DRG. *Pain,* 1998, 78:9–105
41. Olmarker K, Nordborg C, Larsson K, Rydevik B. Ultrastructural changes in spinal nerve roots induced by autologous nucleus pulposus. *Spine* 1996;21:411–4.
42. Olmarker K, Rydevik B, Nordborg C. Autologous nucleus pulposus induces neurophysiologic and histologic changes in porcine cauda equina nerve roots [see comments]. *Spine* 1993;18:1425–32.
43. Otani K, Arai I, Mao G P, Konno S, Olmarker K, Kikuchi S. Nucleus pulposus-induced nerve root injury. The relationship between blood flow and nerve conduction velocity. Manuscript
44. Otani K, Mao G P, Arai I, Konno S, Olmarker K, Kikuchi S. Nucleus pulposus-induced increase in vascular permeability in the nerve root. Manuscript
45. Petrovich M S, Hsu H Y, Gu X, Dugal P, Heller K B, Sadun A A. Pentoxifylline suppression of TNF-alpha mediated axonal degeneration in the rabbit optic nerve. Neurol *Res* 1997; 19:551–4.
46. Pichler W J, Zanni M, von Greyerz S, Schnyder B, Mauri-HeUweg D, Wendland, T. High IL-5 production by human drug-specific T cell clones. *Int Arch Allergy Immunol* 1997; 1 13:177–80.
47. Redford E J, Hall S M, Smith K J. Vascular changes and demyelination induced by the intra neural injection of tumour necrosis factor. *Brain* 1995; 1 18 :869–78.
48. Robache-Gallea S, Bruneau J M, Robbe H, Morand V, Capdevila C, Bhatnagar N, Chouaib S, Roman-Roman S. Partial purification and characterization of a tumor necrosis factor-alpha converting activity. *Eur J Immunol* 1997;27:1275–82.
49. Rosendahl M S, Ko S C, Long D L, Brewer M T, Rosenzweig B, Hedl E, Anderson L, Pyle S M, Moreland J, Meyers M A, Kohno T, Lyons D, Lichenstein H S. Identification and characterization of a pro-tumor necrosis factor-alpha-processing enzyme from the ADAM family of zinc metalloproteases. *J Biol Chem* 1997;272:24588–93.
50. Said G, Hontebeyrie-Joskowicz M. Nerve lesions induced by macrophage activation. *Res Immunol* 1992;143:589–99.
51. Sehnaj K W, Raine C S. Tumor necrosis factor mediates myelin and oligodendrocyte damage in vitro. *Ann Neurol* 1988;23:339–46.
52. Shapira L, Houri Y, Barak V, Halabi A, Soskoine W A, Stabholz A. Human monocyte response to cementum extracts from periodontally diseased teeth: effect of conditioning with tetracycline. *J Periodontol* 1996;67:682–7.
53. Shapira L, Houri Y, Barak V, Soskolne W A, Halabi A, Stabholz A. Tetracycline inhibits' Porphyromonas gingivalis lipopolysaccharide-induced lesions in vivo and TNF α processing in vitro. *J Periodontal Res* 1997;32:183–8.
54. Sharief M K, Ingram D A, Swash M. Circulating tumor necrosis factor-alpha correlates with electrodiagnostic abnormalities in Guillain-Barre syndrome. *Ann Neurol* 1997;42:68–73.
55. Smith C S, Ortega G, Parker L, Shearer W T. Cyclosporin A blocks induction of tumor necrosis factor-alpha in human B lymphocytes. *Biochem BioRhys Res Commun* 1994;204:383–90.
56. Sonuner C, Schmidt C, George A, Toyka K V. A metalloprotease-inhibitor reduces pain associated behaviour in mice with experimental neuropathy. Neurosci Lett 1997;237:45–8.
57. Sorkin L S, Xiao W H, Wagner R, Myers R R. Tumour necrosis factor-alpha induces ectopic activity in nociceptive primary afferent fibres. *Neuroscience* 1997;81:255–62.
58. Steinmeyer J, Daufeldt S, Taiwo Y O. Pharmacological effect of tetracyclines on proteoglycanases from interleukin-1-treated articular cartilage. *Biochem Pharmacol* 1998;55:93–100.
59. Stoll G, Jung S, Jander S, van der Meide P, Hartung H P. Tumor necrosis factor-alpha in immunomediated demyelination and Wallerian degeneration of the rat peripheral nervous system. *Neuroimmunol* 1993;45: 175–82.
60. Takao Y, Mikawa K, Nishina K, Maekawa N, Obara H. Lidocaine attenuates hyperoxic lung injury in rabbits. *Acta Anaesthesiol Scand* 1996;40:318–25.
61. Teoh K H, Bradley C A, Galt J, Burrows H. Steroid inhibition of cytokine-mediated vasodilation after warm heart surgery. *Circulation* 1995;92:II347–53.
62. Tsukamoto T, Ishikawa M, Yamamoto T. Suppressive effects of TNF-α on myelin formation in vitro. *Acta Neurol Scand* 1995;91:71–5.
63. van der Poll T, Jansen P M, Van Zee K J, Welborn M Br, de Jong I, Hack C E, Loetscher H, Lesslauer W, Lowry S F, Moidawer L L. Tumor necrosis factor-alpha induces activation of coagulation and fibrinolysis in baboons through an exclusive effect on the p55 receptor. *Blood* 1996;88:922–7.
64. Villarroya H, Violleau K, Ben Younes-Chennoufi A, Baumann N. Myelin-induced experimental allergic encephalomyelitis in Lewis rats: tumor necrosis factor alpha levels in serum of cerebrospinal fluid immunohistochemical expression in glial cells and neurophages of optic nerve and spinal cord. *J Neuroimmunol* 1996;64:55–61.
65. Wagner R, Myers R R. Schwann cells produce tumor necrosis factor alpha: expression in injured non-injured nerves. *Neuroscience* 1996;73:625–9.
66. Wagner R, Myers R R. Endoneurial injection of TNF-α produces neuropathic pain behaviours. *Neuroreport* 1996;7:2897–901.
67. Wasaki S, Sakaida I, Uchida K, Kiinura T, Kayano K, Okita K. Preventive effect of cyclosporin A on experimentally induced acute liver injury in rats. Liver 1997; 17:107–14.

68. Wershil B K, Furuta G T, Lavigne J A, Choudhury A R, Wang Z S, Galli S J. Dexamethasone cyclosporin A suppress mast cell-leukocyte cytokine cascades by multiple mechanisms. *Int Arch Allerg Immunol* 1995;107:323–4.
69. Yabuki S, Kawaguchi Y, Olmarker K, Rydevik B. Effects of lidocaine on nucleus pulposus-induced nerve root injury. *Spine,* 1998, 23:29:2383–89
70. Zhu J, Bai X F, Mix E, Link H. Cytokine dichotomy in peripheral nervous system influences the outcome of experimental allergic neuritis: dynamics of MRNA expression for IL-1 beta, IL-6, IL-10, IL-12, TNF-α, TNF-beta, and cytolysin. *Clin Immunol Immunuopathol* 1997;84:85–94.

What is claimed is:

1. A method of treating a nerve disorder mediated by nucleus pulposus in a mammal in need of such treatment, wherein said nerve disorder mediated by nucleus pulposus is caused by the liberation of TNF-α and compounds triggerd by the liberation of or presence of TNF-α, comprising the step of:

(A) administering a TNF-α inhibitor, wherein said TNF-α inhibitor is (i) a soluble cytokine receptor that blocks TNF-α activity, (ii) a monoclonal antibody that blocks TNF-α activity, or (iii) a tetracycline or a chemically modified tetracycline that blocks TNF-α activity, to said mammal in need of such treatment thereby inhibiting TNF-α and treating said disorder.

2. The method of claim 1, wherein the mammal is human.
3. The method of claim 1, wherein the tetracycline or chemically modified tetracycline is selected from the group consisting of: tetracycline, doxycycline, lymecycline, oxytetracycline, minocycline, dedimethylaminotetracycline and bases and salts thereof.
4. The method of claim 1, wherein said nerve disorder is nerve root injury.
5. The method of claim 4, wherein said nerve disorder involves pain.
6. The method of claim 4, wherein the mammal is human.
7. The method of claim 4, wherein the tetracycline or chemically modified tetracycline is selected from the group consisting of: tetracycline, doxycycline, lymecycline, oxytetracycline, minocycline, dedimethylaminotetracycline and bases and salts thereof.
8. The method of claim 4, wherein said TNF-alpha inhibitor is administered systemically or locally.
9. The method of claim 4, wherein said TNF-alpha inhibitor is administered parenterally.
10. The method of claim 4, wherein said TNF-alpha inhibitor is administered intramuscularly (i.m.), intravenously (i.v.), subcutaneously (s.c.) orally or rectally.
11. The method of claim 10, wherein said TNF-alpha inhibitor is administered i.v. by injection or infusion.
12. The method of claim 10, wherein said TNF-alpha inhibitor is administered orally at a dosage of about 20 mg to about 1,500 mg.
13. The method of claim 4, wherein said TNF-alpha inhibitor is tetracycline and is administered at a dosage of about 100 mg.
14. The method of claim 1, wherein said nerve disorder is caused by a herniated disc.
15. The method of claim 14, wherein said nerve disorder involves pain.
16. The method of claim 14, wherein the mammal is human.
17. The method of claim 14, wherein the tetracycline or chemically modified tetracycline is selected from the group consisting of: tetracycline, doxycycline, lymecycline, oxytetracycline, minocycline, dedimethylaminotetracycline and bases and salts thereof.
18. The method of claim 14, wherein said TNF-alpha inhibitor is administered systemically or locally.
19. The method of claim 14, wherein said TNF-alpha inhibitor is administered parenterally.
20. The method of claim 14, wherein said TNF-alpha inhibitor is administered intramuscularly (i.m.), intravenously (i.v.), subcutaneously (s.c.) orally or rectally.
21. The method of claim 20, wherein said TNF-alpha inhibitor is administered i.v. by injection or infusion.
22. The method of claim 20, wherein said TNF-alpha inhibitor is administered orally at a dosage of about 20 mg to about 1,500 mg.
23. The method of claim 14, wherein said TNF-alpha inhibitor is tetracycline and is administered at a dosage of about 100 mg.
24. The method of claim 1, wherein said nerve disorder presents as sciatica.
25. The method of claim 24, wherein the mammal is human.
26. The method of claim 24, wherein the tetracycline or chemically modified tetracycline is selected from the group consisting of: tetracycline, doxycycline lymecycline, oxytetracycline, minocycline, dedimethylaminotetracycline and bases and salts thereof.
27. The method of claim 24, wherein said TNF-alpha inhibitor is administered systemically or locally.
28. The method of claim 24, wherein said TNF-alpha inhibitor is administered parenterally.
29. The method of claim 24, wherein said TNF-alpha inhibitor is administered intramuscularly (i.m.), intravenously (i.v.), subcutaneously (s.c.) orally or rectally.
30. The method of claim 29, wherein said TNF-alpha inhibitor is administered i.v. by injection or infusion.
31. The method of claim 29, wherein said TNF-alpha inhibitor is administered orally at a dosage of about 20 mg to about 1,500 mg.
32. The method of claim 24, wherein said TNF-alpha inhibitor is tetracycline and is administered at a dosage of about 100 mg.
33. The method of claim 1, wherein said nerve disorder involves pain.
34. The method of claim 1, wherein said TNF-α inhibitor is administered systemically or locally.
35. The method of claim 1, wherein said TNF-α inhibitor is administered parenterally.
36. The method of claim 1, wherein said TNF-α inhibitor is administered intramuscularly (i.m.), intravenously (i.v.), subcutaneously (s.c.), orally or rectally.
37. The method of claim 36, wherein said TNF-α inhibitor is administered i.v. by injection or infusion.
38. The method of claim 36, wherein said TNF-α inhibitor is administered orally at a dosage of about 20 mg to about 1,500 mg.
39. The method of claim 1, wherein said TNF-α inhibitor is a tetracycline and is administered at a dosage of about 100 mg.

* * * * *